(12) United States Patent
Kulkarni (10) Patent No.: US 12,181,471 B2
(45) Date of Patent: Dec. 31, 2024

(54) DEVICES AND METHODS OF URINALYSIS FOR REAL-TIME MONITORING OF ORGAN HEALTH

(71) Applicant: SciKare, Inc., Goleta, CA (US)

(72) Inventor: Prajakta Kulkarni, Goleta, CA (US)

(73) Assignee: SCIKARE, INC., Santa Barbara, CA (US)

( * ) Notice: Subject to any disclaimer, the term of this patent is extended or adjusted under 35 U.S.C. 154(b) by 0 days.

(21) Appl. No.: 18/176,144

(22) Filed: Feb. 28, 2023

(65) Prior Publication Data

US 2023/0204571 A1    Jun. 29, 2023

Related U.S. Application Data

(63) Continuation-in-part of application No. 17/940,565, filed on Sep. 8, 2022, now abandoned, which is a
(Continued)

(51) Int. Cl.
*G01N 33/543* (2006.01)
*A61B 10/00* (2006.01)
*E03D 9/00* (2006.01)

(52) U.S. Cl.
CPC ....... *G01N 33/5438* (2013.01); *A61B 10/007* (2013.01); *E03D 9/00* (2013.01)

(58) Field of Classification Search
CPC ........ G01N 33/48; G01N 33/50; G01N 33/53; G01N 33/543; G01N 33/54366;
(Continued)

(56) References Cited

U.S. PATENT DOCUMENTS

| 4,466,445 A | 8/1984 | Abrams |
| 6,572,830 B1* | 6/2003 | Burdon ............... B01J 19/0093 422/129 |

(Continued)

FOREIGN PATENT DOCUMENTS

| EP | 0342028 A2 | 11/1989 |
| WO | 2009035599 A1 | 3/2009 |

*Primary Examiner* — Christopher L Chin
*Assistant Examiner* — Christina Lusi
(74) *Attorney, Agent, or Firm* — SoCal IP Law Group LLP; Guy Cumberbatch (57) ABSTRACT

A non-invasive system and method for disease detection and real-time monitoring of organ health wherein the changes in the electrical properties of urine samples are studied over time in the presence or absence of interacting chemicals for qualitative and quantitative estimation of urinary analytes. The system has two components—a test platform and a reader. The test platform is integrated with electrodes and chemicals, which interact with urine to detect the biomarker of the disease and quantify the analyte. The changes in the electrical properties serve as an electrical signature for a particular analyte. This electrical signal from the test platform is relayed to an electronic reader that receives, processes, and analyzes the data for single test detection or continuous monitoring. The reader stores the information that can then be coupled to a readout system or transmitted by wired or wireless mechanisms to any electronic platform in real-time.

25 Claims, 8 Drawing Sheets

Related U.S. Application Data continuation of application No. PCT/US2021/021763, filed on Mar. 10, 2021.

(60) Provisional application No. 62/987,716, filed on Mar. 10, 2020.

(58) Field of Classification Search
CPC ......... G01N 33/54373; G01N 33/5438; G01N 1/00; G01N 2001/002; G01N 35/00; G01N 33/493; G01N 27/00; G01N 27/128; G01N 27/30; G01N 27/44791; G01N 27/327; G01N 27/3272; G01N 27/22; A61B 10/00; A61B 10/0045; A61B 10/007; A61B 5/20; A61B 5/201; A61B 5/202; A61B 5/207; B01L 3/00; B01L 3/50; B01L 3/502; B01L 3/5025; B01L 3/5027; E03D 9/00
USPC ......... 436/150; 422/502, 504, 507; 204/403.01, 403.02, 403.03, 403.13
See application file for complete search history.

(56) References Cited

U.S. PATENT DOCUMENTS

| | | | |
|---|---|---|---|
| 7,755,497 | B2 | 7/2010 | Wada et al. |
| 9,457,041 | B2 | 10/2016 | Kulkarni et al. |
| 11,287,415 | B2 | 3/2022 | Barakat et al. |
| 2003/0109805 | A1 | 6/2003 | Ito et al. |
| 2004/0067164 | A1 | 4/2004 | VanBrunt et al. |
| 2004/0132220 | A1 | 7/2004 | Fish |
| 2005/0261605 | A1 | 11/2005 | Shemer et al. |
| 2008/0185295 | A1 | 8/2008 | Briman et al. |
| 2011/0060299 | A1 | 3/2011 | Wada et al. |
| 2013/0041236 | A1* | 2/2013 | Pugia .................... B01L 3/5027 422/430 |
| 2016/0051176 | A1 | 2/2016 | Ramos et al. |
| 2016/0116427 | A1* | 4/2016 | Laurenson ............... B05D 5/00 427/2.13 |
| 2018/0242957 | A1 | 8/2018 | Tariyal et al. |
| 2020/0008299 | A1* | 1/2020 | Tran ..................... H05K 1/0386 |
| 2021/0003564 | A1* | 1/2021 | Rao ..................... C12N 9/0006 |

\* cited by examiner

DEVICES AND METHODS OF URINALYSIS FOR REAL-TIME MONITORING OF ORGAN HEALTH

RELATED APPLICATION INFORMATION

The present application is a continuation-in-part of application Ser. No. 17/940,565, filed Sep. 8, 2022, which is a bypass continuation of and claims priority from International PCT Patent Application No. PCT/US21/21763, filed Mar. 10, 2021, which claims priority under 35 U.S.C. 119 to U.S. Provisional Application Ser. No. 62/987,716, filed Mar. 10, 2020, all entitled, "METHODS OF URINALYSIS FOR REAL-TIME MONITORING OF ORGAN HEALTH," and the contents of which are expressly incorporated herein by reference.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

Field

This disclosure relates to devices and methods for disease detection and real-time monitoring of organ health wherein the changes in the electrical properties of urine samples are studied over time in the presence or absence of interacting chemicals.

Description of the Related Art

The urinary biomarkers are analyzed to detect diseases and monitor health at home, in clinics, and the pathology labs. Home-based tests that are currently available for use are mostly qualitative or semi-quantitative in nature. But more precise and reliable information about the disease and overall health can be gathered with quantitative urinalysis.

The quantitative urine analysis conducted in the pathology labs requires skilled personnel to operate the instrument and does not perform real-time organ health monitoring. Hence, smart toilets have been developed to detect urine [CN109870565], monitor fluid body volume in the predetermined time [CA3094993], and sense biomarkers using aptamers [US20180321218]. But the technologies need further development to be able to handle the extensive tests that come under the umbrella of urinalysis.

Systems for monitoring the medical status of patients at home from a care center are also advancing, which can transmit the information from the patient at a remote location to the doctors' clinic. [WO1994024929] A kidney health monitoring system was also developed in a similar manner [US20180110455].

Instruments for automated urine analysis often use optical sensors to conduct colorimetric, fluorometric, infrared, and turbidimetric analysis. However, these technologies are restricted in practice due to the nature of the tests and the cost associated with the devices. Electrochemical tests are highly precise, and some tests have shown lower limits of detections as compared to colorimetric and fluorometric methods. However, there is no home-based device that can conduct automated, quantitative urinalysis due to the lack of a usable test platform and method for integrating existing setups with advancing technologies. This invention describes the use of test platforms integrated with electrodes and chemicals for sensing the electrical behavior of urinary analytes in the presence of reactive chemicals.

SUMMARY OF THE INVENTION

According to exemplary embodiments, a device for conducting automated urine analysis for detecting and monitoring organ health is provided.

The exemplary kidney health monitor in this invention is designed for continuous, real-time monitoring of kidney health. It analyses biomarkers in the urine by employing electrochemical tests and detects the onset of kidney disease earlier than widely used kidney function tests. It also monitors kidney health to determine the kidney damage and extent of kidney failure. This device has a disposable part that interacts with urine, carries out a test, records signature behaviors of analytes in the form of an electrical signal, and relays information to a non-disposable receiver. This receiver can then transmit the information to other devices for analysis.

The test platform described in this invention can act as an accessory or a substitute to prior art systems for sequential and simultaneous analysis of urinary biomarkers. Moreover, the current invention can be built as a flushable system which differentiates it from the previous inventions.

Other features and characteristics of the present invention, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

DETAILED DESCRIPTION

Unless defined otherwise, all terms of art, notations, and other technical terms or terminology used herein have the same meaning as is commonly understood by one of ordinary skilled in the art to which this disclosure belongs. All patents, applications, published applications, and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the invention and are not intended to be limiting.

Device for Automated, Real-Time Urine Analysis

The device records the signature electrical behaviors of analytes in the presence of specific electrochemical to detect and quantify the biomarker and processes the data for the purpose of diagnosis or monitoring organ health. A kidney health monitoring test platform is developed as an example of the present invention.

The device has two major components—
1. Disposable test platform—interacts with urine, pumps in the urine for a transient period using tubing and microfluidic channels distribute the collected sample to different test wells. It is equipped with electrodes and chemicals to carry out the analysis. The disposable part has conductive traces or is connected to PCB to relay the information to the electronic non-disposable part.
2. Non-disposable Reader—The electrical signal collected from the disposable test platform is stored and processed in the reader in the predetermined format and is transmitted by a wired or wireless mechanism to any electronic platform.

Exemplary Development of Kidney Health Monitoring Device

The present application provides an exemplary development of a non-invasive device to monitor renal health. This device detects and quantifies analytes excreted by kidneys to determine the stage of renal failure and other diseases associated with renal function impairment. The device can conduct a simultaneous estimation of multiple analytes by employing electrochemical tests and records the electrical behavior of the biomarkers in healthy and disease conditions. The device acts as a 24-hour (or continuous) urine sample analyzer to perform the kidney function tests, quantifies proteins (microalbumin, protein biomarkers), proteases and gelatinases, creatinine, urea, ions (calcium, potassium, sodium), a ratio of protein to creatinine and creatinine to urea to estimate the extent of kidney function impairment or renal failure.

The Device Can Be Made as a Single-Use Device

Figure 1:
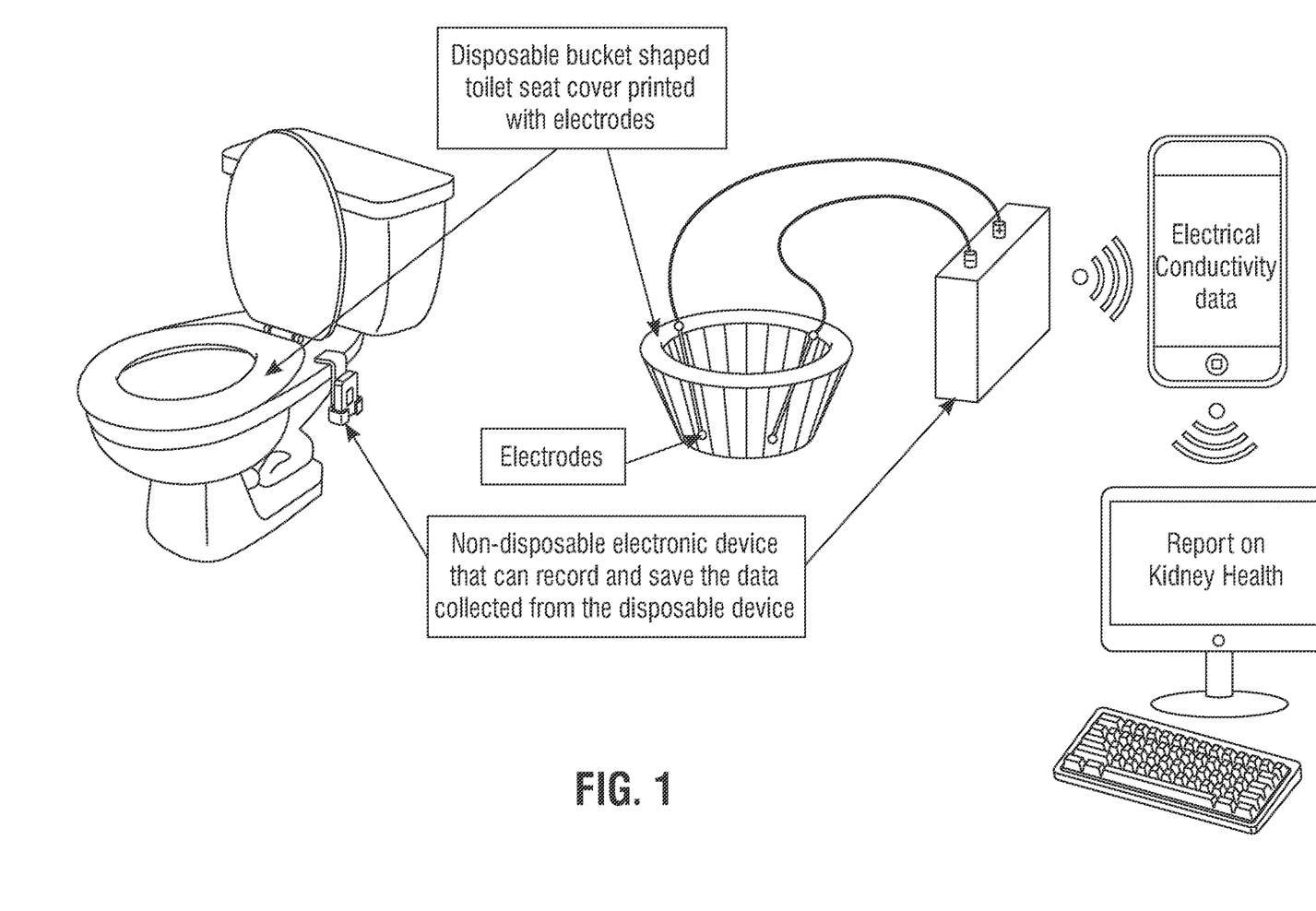
FIG. 1 is a schematic diagram of the components in an exemplary system for kidney health monitoring system.

FIG. 1 is a schematic diagram of the components for and use of an exemplary system for kidney health monitoring. The device can be installed on a toilet bowl (A). The disposable part of the test platform is placed on or under the toilet seat (B) designed explicitly with electrodes and conductive traces (B). It is then connected to the non-disposable electronic device (wirelessly or wired) to record, monitor, and save the data (C). This device then transmits the electrical conductivity data to an electronic device (D) such as a smartphone or tablet that can then further analyze or transmit the data to another electronic device to estimate the stage of the kidney disease and other urine tests required for the determination of kidney function. (Steps B, C, and D can be combined in the same device) The C and D are separate in this example. However, the functionality can be combined in one part.

The test platform in the form of collection basket shaped to fit in a toilet or urinal may be disposable, such as made of paper with the electrodes and conductive traces printed on the paper, and the entire the collection basket is flushable. Alternatively, the collection basket is made of a non-flushable material and the basket is configured to remain in the toilet bowl over a period of time and perform multiple tests and record changes in the electrical behavior of the urine analytes.

In other words, the test platforms can be made disposable or flushable. Flushable platforms are desirably made up of paper with different chemical compositions. The paper is patterned with hydrophobic layer and dissolvable paper. The parts of the paper carry the printed electrodes and the chemicals on the surface of the hydrophobic and hydrophilic areas. The chemicals dissolve when they come in contact with urine sample and allow the reaction to happen. Within the same time, dissolvable paper patterned on the paper disintegrates and the paper loses its integrity. The change in the pH caused by the reactions and dissolved paper is neutralized by the coated chemicals on the paper and allow flushable device to be used on the toilet bowl.

Disposable materials used in the invention include any materials considered to be compatible with urine testing under consideration. The disposable collector may be made up of, but not restricted to materials polypropylene, polystyrene, polyethylene, metal, PDMS, and paper with or without hydrophobic coatings.

Figures 2A, 2B:
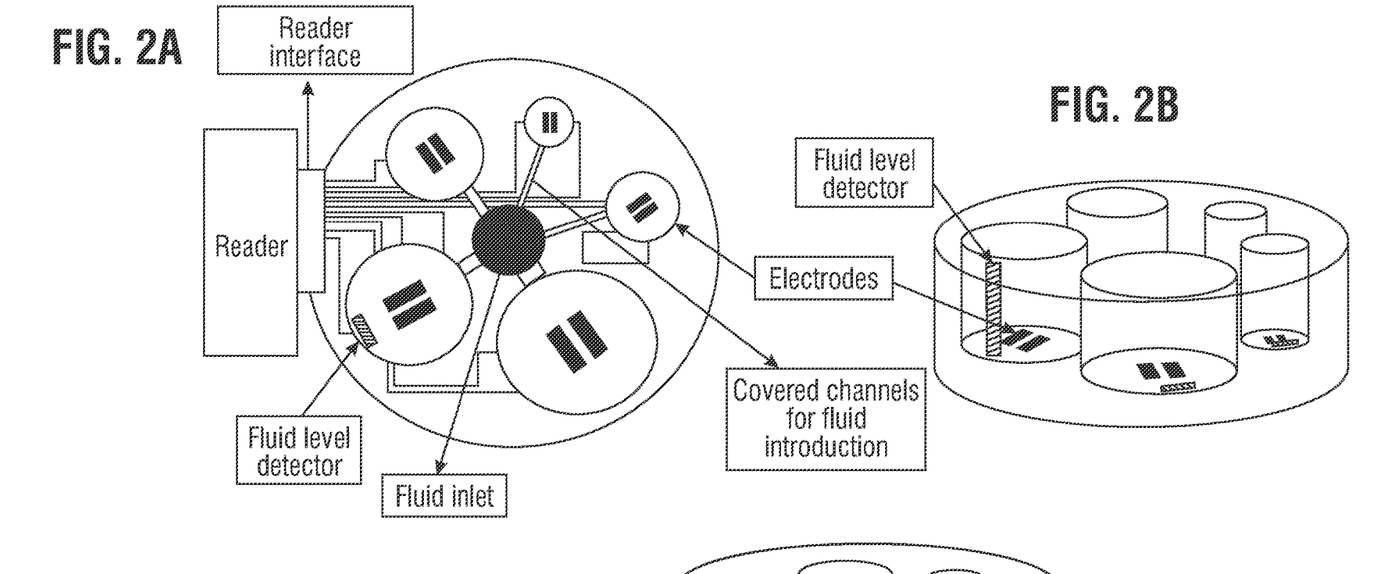
FIGS. 2A, 2B and 2C are several configurations of an exemplary test platform with multiple test wells.
Figure 2C:
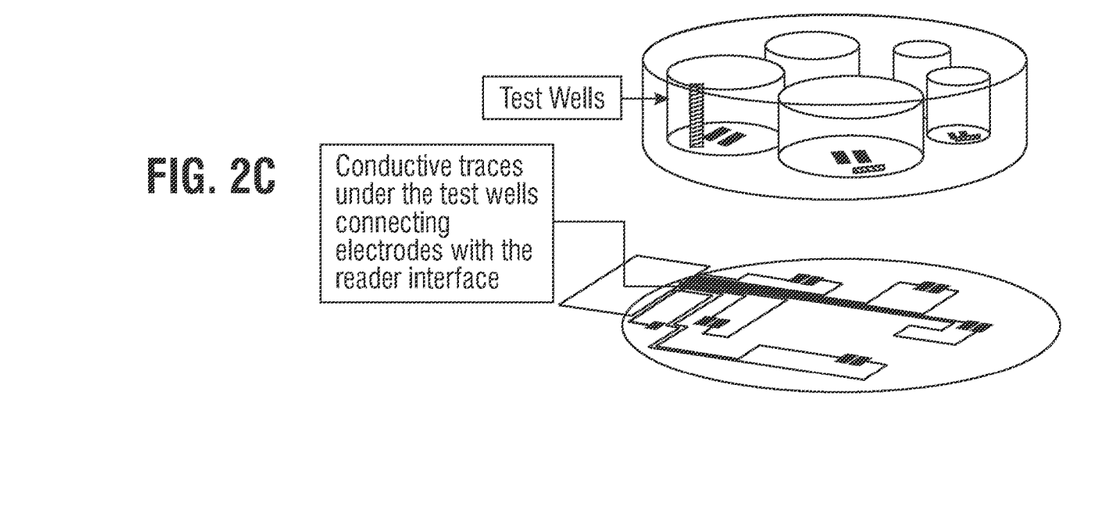

FIGS. 2A, 2B, 2C describe scenarios in which multiple tests are conducted on one disposable test platform (A) equipped with electrodes and fluid detectors (B) which are placed on a conductive platform to detect the electrical signatures of the analytes. The test platform has a number of microfluidic distribution channels for uneven distribution of the urine sample to different locations for simultaneous determination of multiple analytes using one urine sample test wells for the purpose of conducting tests simultaneously. The device in the figure has five test wells comprising a pair of electrodes in each test well. The test platform includes test wells for collecting urine, and each test well is composed of Polydimethylsiloxane (PDMS), but any other water repellant material can be used.

The test wells are made with different diameters to accommodate different volumes of the test samples on the same platform. Each test well is attached to the fluid inlet by microfluidic channels of depth 500μ, and widths of 100 μm, 200 μm, 250 μm, 350 μm, and 500 μm for uneven distribution of the fluid to respective test wells in a given time. The number, length, width and/or height (dimensions) of microfluidic distribution channels that are open for urine flow can be increased or decreased based on test requirements. In this example, the smallest well of volume 0.2 mL was used for estimation of ions and the largest well of volume 0.8 mL was used for quantitative estimation of total proteins. A level detector may be attached to the device to further calculate the volume of the sample in each well of the known radius.

The test wells are either coated with an electrochemical, and a conductive polymer or electrochemical is introduced into the device through the fluid inlet port. For instance, the surface of the platform including all test wells may be coated with chemicals required for electrochemical test and polymeric conductive materials. The platform can be coated with hydrophilic materials which could be mixtures of electrolytes, reactants, stabilizers, preservatives and other ionic or non-ionic molecules and polymers. Any available coating methods for such mixtures are covered under this invention. Wells on the platform can also be coated with the same or variable composition of the chemical mixtures to suit the need of the chemical analysis. When the wells are made up of the materials incompatible with the coating techniques, a fast release tablet or effervescent granule made up of reactants, proteins, biologicals, excipients and conductive polymers can be used.

Each well contains pair of electrodes inside the well, which are connected to the reader interface by conductive traces. The fluid inlet port is located at the center of the device to distribute the fluid to all the test wells via covered microfluidic channels. The test platform is activated as it comes in contact with urine distributed through each channel. The channels indicated in the figures are conceptual representations of the micro sized channels. The channels can be shaped differently than linear; e.g., edged, serpentine, V-shaped or U-shaped. But the top and bottom surfaces of the microfluidic channels should be closed so that fluid in the channels is not exposed directly to air to avoid unintended evaporation of the fluid. While designing the paper-based system, the hydrophilic part of the paper channels is lined with millimeter sized plastic films on the surface (1 mm or more in breadth and with variable lengths). In the paper-based based designs the capillary action and the hydrophilic coating on the paper determines the rate of the fluid flow within the channel. The use of such samples for altering the flow rate and successfully conducting simultaneous and sequential chemical analysis is one aspect of this application.

As the fluid is filled in the wells, the conductivity of the sample is tested, and the information is transferred to the reader interface. The conductivity of the fluid in each well is monitored and recorded such as after every 20 seconds, and the data is recorded for a predetermined time which is a minimum of 20 seconds up to 24 hours. The data is then analyzed by the reader based on the signal ranges stored on the device. As an example, the test platform is composed of PDMS, and the electrodes are immersed in the test wells during the process of curing. The chemicals are introduced to the wells through the fluid inlet. The device is then bonded on the PCB to align electrodes with the conductive traces. The PCB is then attached to a multi-probe conductivity analyzer to record the changes in the electrical properties of the sample over time. The data is then analyzed by the reader and is processed to learn linear relationships in changes in conductance over time. The conductance values are converted to the amount of analyte present in the sample. The information is then correlated to the normal ranges of the analytes and stages of the renal disease to detect the disease and estimate the extent of renal function impairment.

Figure 3A:
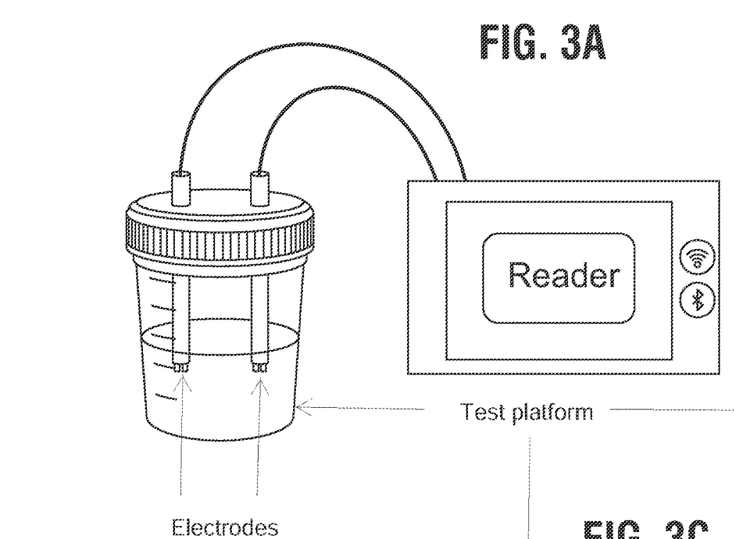
FIGS. 3A, 3B and 3C are several embodiments of a single use cup comprising electrodes.
Figure 3B:
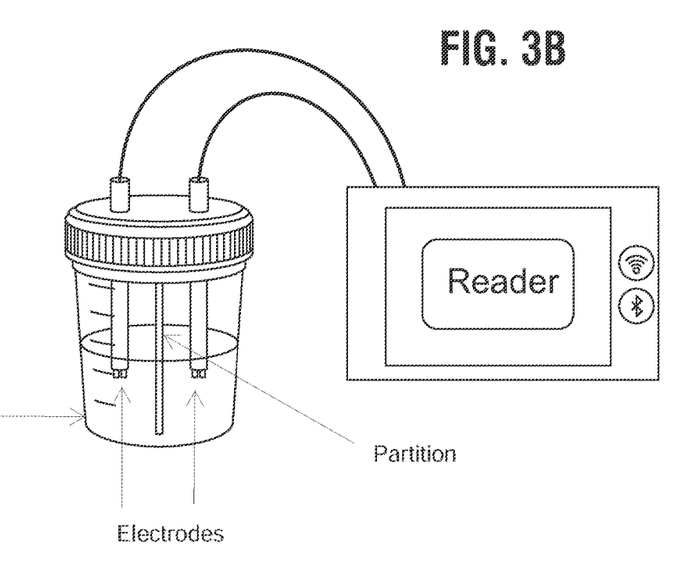
Figure 3C:
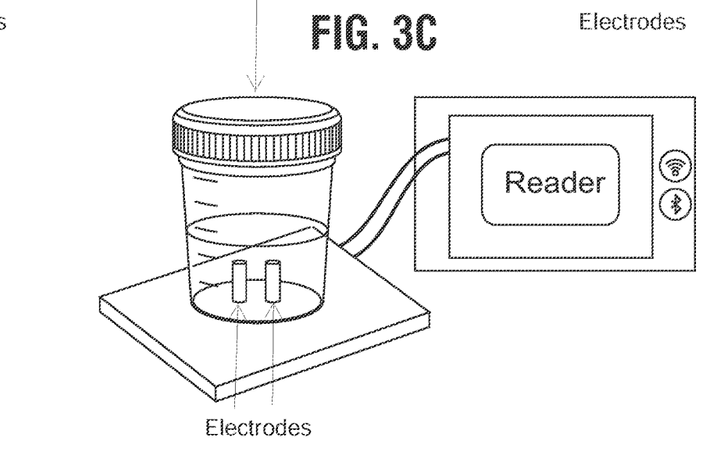

FIGS. 3A, 3B, 3C illustrate alternative forms of the disposable tester. The disposable barrier on this device is the container wall. The cap of the device (A) or the bottom of the device (C) is equipped with electrodes to record the electrical signature of the analytes for qualitative and quantitative estimation of biomarkers. The barrier is divided (B) to create separate environments in the same device. The position of the reader may be changed with respect to the position of the electrodes in the device. In an example, a urine collection cup was used with titanium and platinum electrodes. The lid or the bottom of the container was cut in 1 inch diameter to install the electrodes printed on the PCB. The PCB is physically glued to the container using water-repellant silicon-based glue. The electro chemicals were added to the container, and the baseline conductance is recorded using a multi-probe conductivity measurement device. To this device, urine sample was added, and the conductance was recorded as a function of time. The electrochemical mixtures added to the device vary based on the test. For example, for determination of total urinary proteins, a mixture of NaCl, functionalized PVA, L-arginine were added to the well in molar ratios 2:1:1, and the change is conductance was recorded over time. The reader then processed these electrical signals by subtracting the baseline conductance values from each reading and defining relationship between the conductance over time. We observed linear decrease in the conductance over time in response to the presence of urinary proteins. Similarly, when the tests were conducted for determination of ions, the increase in conductance over time was observed. In all the tests, the rate of reaction determines the duration of the test. For example, the total ions can be estimated within 30 seconds. But the test for total proteins may require recording times longer than 2 minutes. The data is then collected by the reader for further processing.

Figure 4:
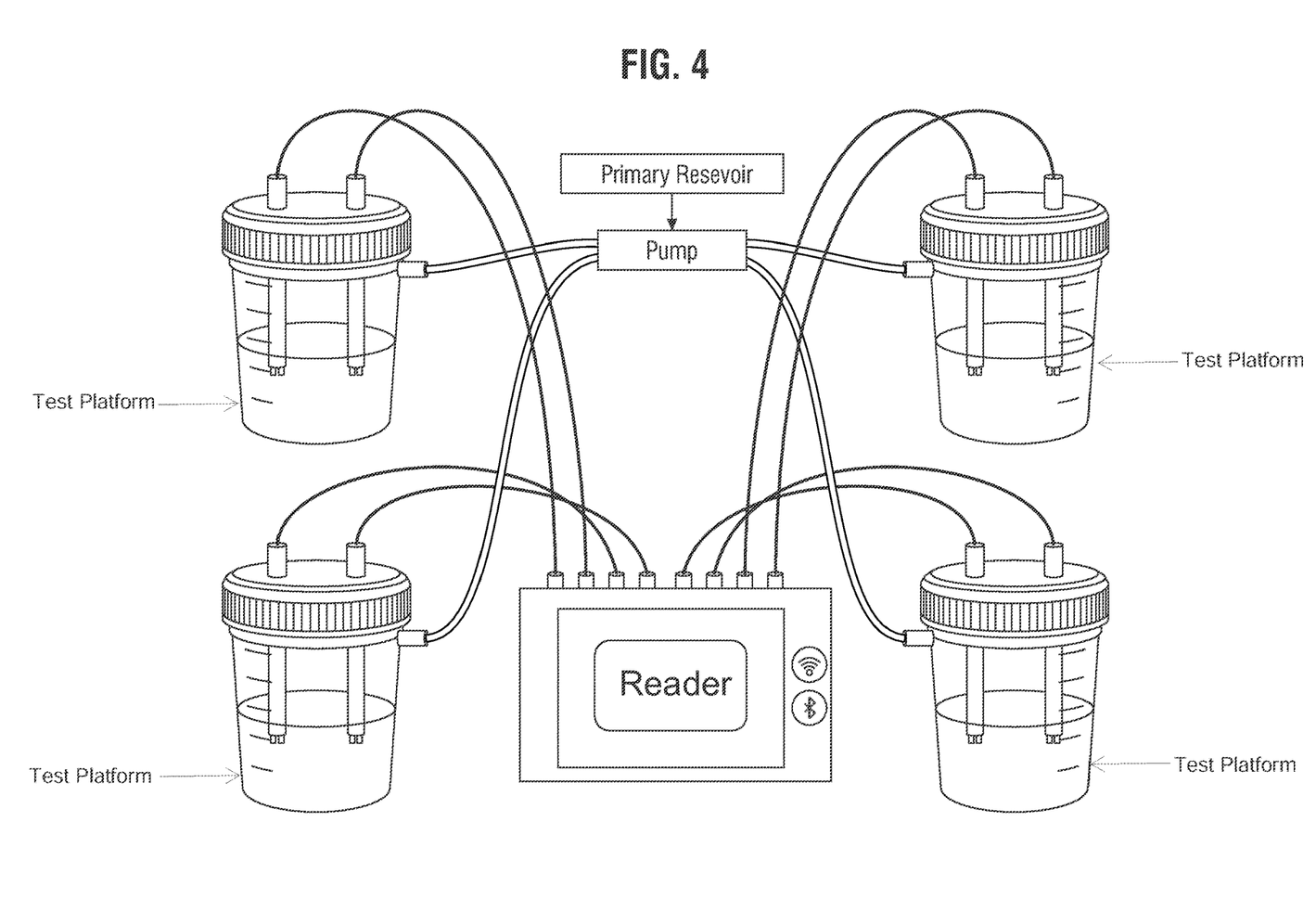
FIG. 4 shows a number of test containers or test wells for recording multiple reactions in series or parallel.

FIG. 4 depicts another alternative scenario for the test platform where larger volumes of the test sample are needed for the test. The primary reservoir, in this case, may be a toilet bowl, urinal, or another container or equipment. The fluid is pumped into the test containers or test wells equipped with the electrolytes and connected to the reader. The tests can be conducted simultaneously or in series.

Simultaneous Measurements

The devices in FIGS. 2, 3, and 4 are used for conducting multiple tests or repeats of the same test. The electrochemical composition for each test is based on the time required to obtain the results. The device conducts measurements in sequence for each parameter based on time to reduce the errors in interpretation. For example, the results for the volume and temperature are obtained instantaneously. The results for total urinary proteins can be obtained in 2 minutes while we wait for 5 minutes to detect the presence of proteolytic enzymes. The computation for the test results for each test occurs at once. But the data for each test is stored as recorded. The system is developed for the measurement of six parameters simultaneously. But it can be designed and used for measuring a single parameter.

Figure 5:
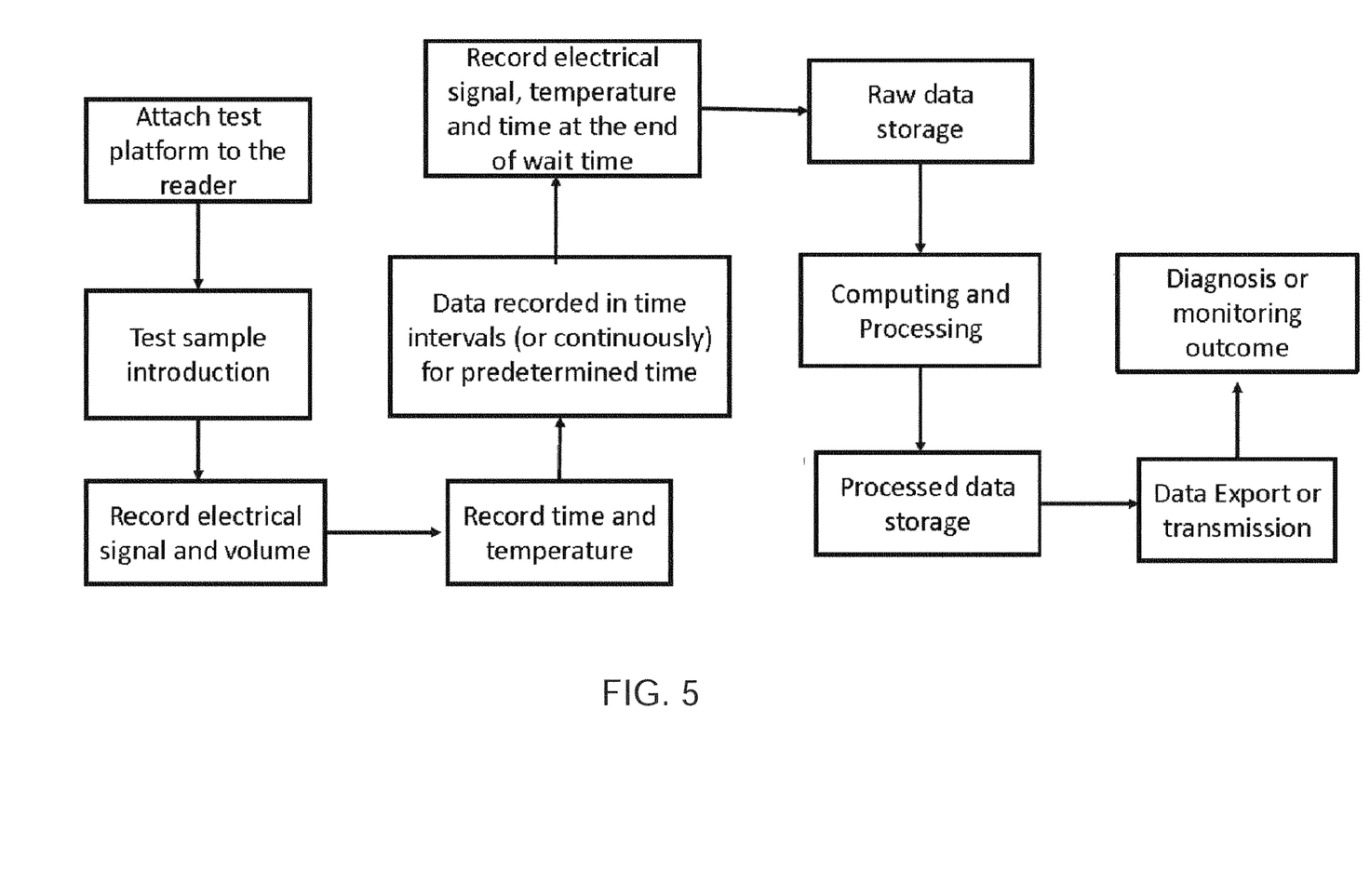
FIG. 5 is a flow chart for a one-time point, single parameter test using the device.
Figure 6:
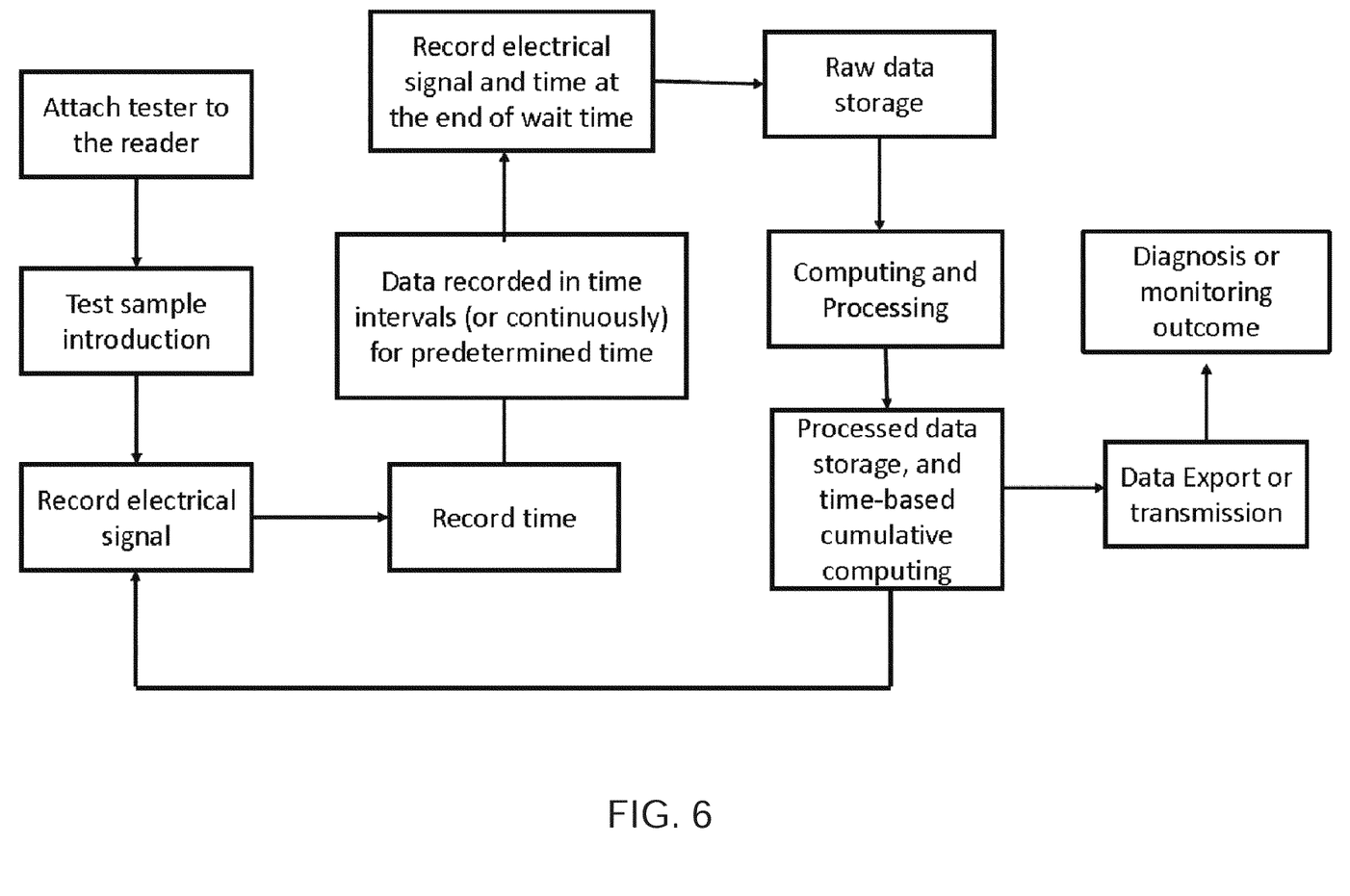
FIG. 6 is a flow chart for a single parameter continuous monitoring.
Figure 7:
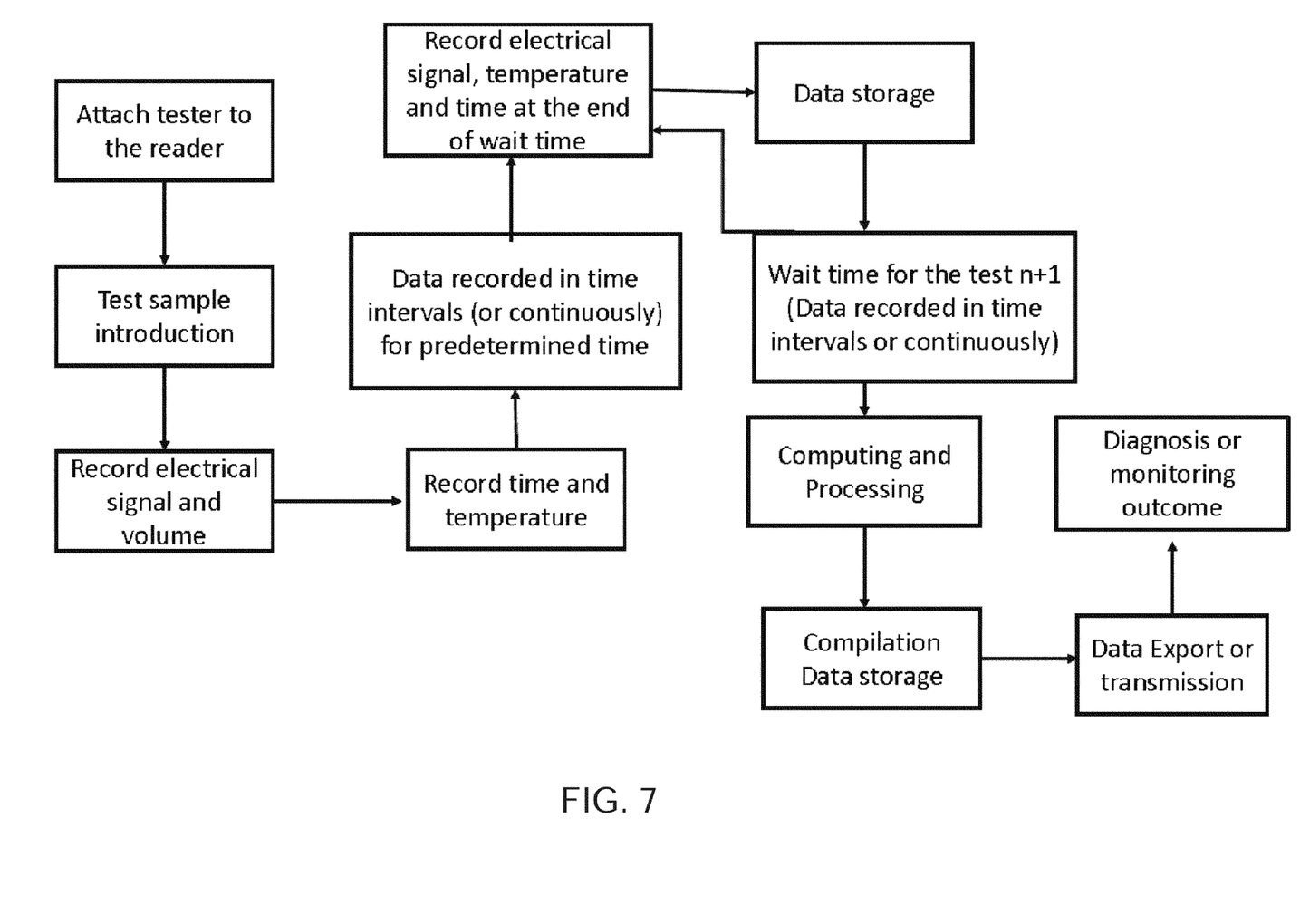
FIG. 7 is a flow chart for a multiple parameter one-time test.
Figure 8:
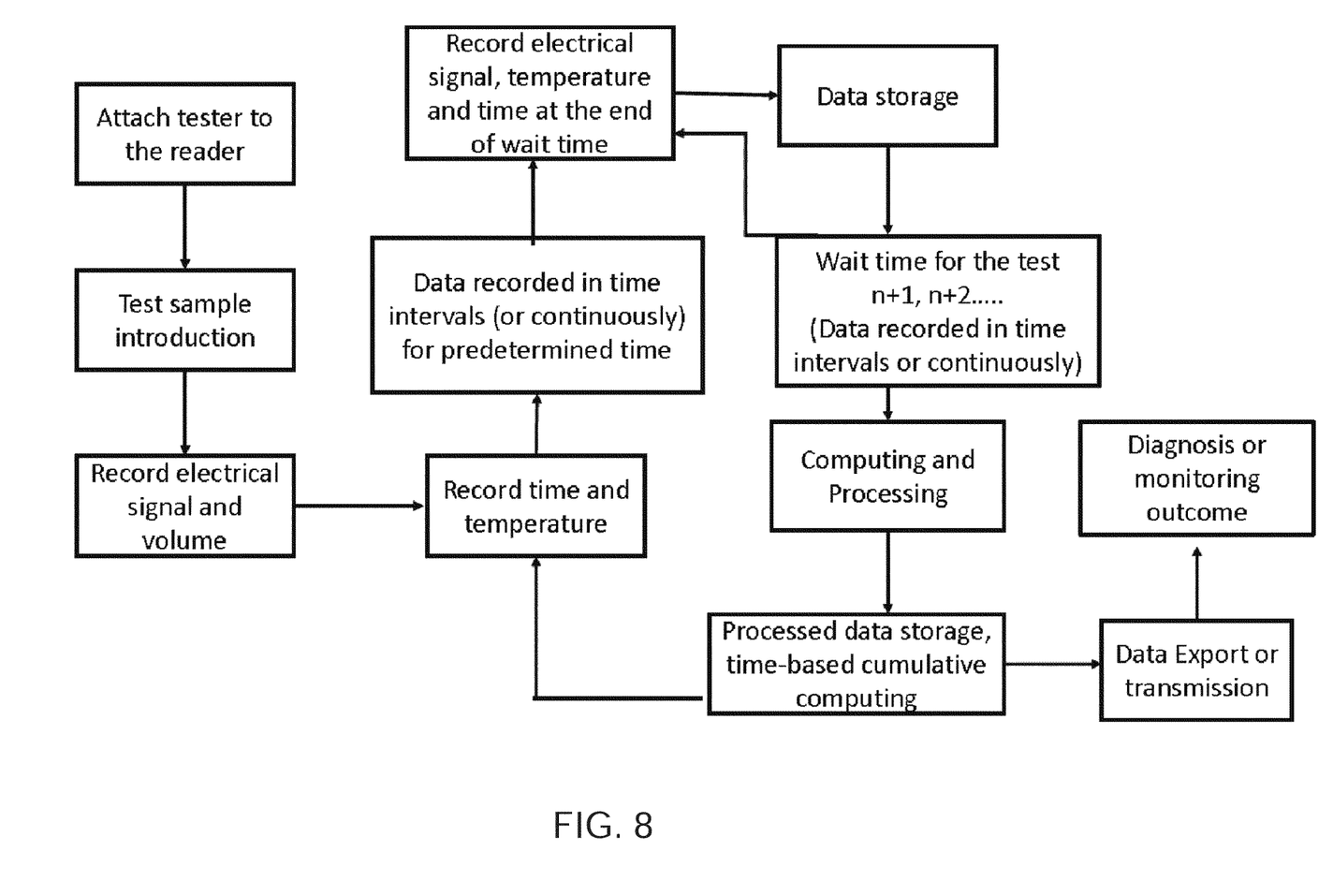
FIG. 8 is a flow chart for continuous monitoring of multiple parameters.

FIG. 5 shows the signal pathway from the device to the diagnostic outcome when a single test is to do for a single parameter. FIG. 6 gives the process of monitoring a single parameter continuously over a predetermined time. FIG. 7 shows the signal path for the scenario where multiple parameters are being analyzed at the sample time for a one-time sample. FIG. 8 shows the process of monitoring multiple parameters at multiple time points or for the purpose of continuous monitoring. In an example, this method is used for simultaneous estimation of urinary protein, creatinine, and calcium over a 24-hour urine sample. The cumulative values were compared with the normal ranges of the analytes to diagnose a disease condition.

Computation of Individual Test Results

The time-dependent changes in the electrical signal detect and quantify the analytes in the urine. The tester runs single or multiple tests simultaneously. The receiver saves the data as it is generated with respect to time. However, the computation takes place for each test in a sequential manner. This helps in the estimation of multiple components from the same tester and also allows time-dependent estimation of analytes as required in 24-hour urine tests or for continuous analysis. The sequence of computation is dependent on the required test panel. For example, for the determination of protein creatinine ratio, the signal from the protein test is recorded and computed for 3 minutes. The signal from the channel for the creatine test is recorded and computed after 1 minute. In both, the test time starts when the urine sample fills into the respective test wells. The computation of the test starts after 3 minutes when the electrical signals for both the tests are available. The data is then processed to find the linear relationship between electrical signal and time. The electrical signal is then converted to values in mg/dl, and then the ratio of the amounts is computed. In some cases, filters can be employed to reduce the noise. Every sample can be measured with an on-off switch or a proximity sensor, and then the device can add the values over 24 hours to give a reading for a 24-hour urine test.

Data Interpretation

The data interpretation is made based on the available known values for the analytes in the urine samples. The data is then presented using an electronic platform in the form of values of each analyte and stage of kidney disease. The presence of more than 300 mg of albumin in 24 hours was considered as kidney damage. The amounts less than 30 mg were considered as a normal range. For a single point determination, the values of microalbumin were correlated with values obtained from the urinary creatinine test to estimate the extent of renal function impairment. The universally used normal ranges were used in all the tests performed. On the multi-test platform, if only one analyte is outside the normal range, the stage of renal failure is not calculated, but the information is highlighted on the reader, indicating requirements for further analysis. For example, matrix metalloproteinases are increased in other chronic diseases and may not necessarily indicate advanced kidney disease. In these cases, the abnormalities in the values will be indicated, but other tests will be suggested to complete the diagnosis.

Transmission of the Data

The data can be transmitted directly from the disposable part of the device or the non-disposable reader. For reliable results, data is transmitted from the reader to an electronic platform. The data can be transferred by a wired connection, Bluetooth, or by a wireless connection to store on a cloud-based platform or a server using any means of existing or novel data transfer protocols.

The intended application of the device:
1. Urinalysis using electrical and electrochemical methods.
2. Monitoring organ health using electrochemical methods of urinalysis in the toilet bowl, urinals, or urine collection containers where electrodes are integrated with the surface or within an accessory.
3. Early detection of diseases with urinalysis when biomarkers show changes in electrical behavior in the presence of a specific electrochemical.
4. Continuous real-time monitoring of organ health in clinics and at home using the electrode embedded devices for urine analysis.

Closing Comments.

While the present invention has been described and shown in considerable detail with reference to certain illustrative embodiments, including various combinations and sub-combinations of features, those skilled in the art will readily appreciate other embodiments and variations and modifications thereof as encompassed within the scope of the present invention.

Moreover, the descriptions of such embodiments, combinations, and sub-combinations are not intended to convey that the invention requires features or combinations of features other than those expressly recited in the claims. Accordingly, the present invention is deemed to include all modifications and variations encompassed within the spirit and scope of the following appended claims.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the methods described herein. Acts, elements, and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising," "including," "carrying," "having," "containing," "involving," and the like are to be understood to be open-ended, i.e., to mean including but not limited to. Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It is claimed:

1. A system for electrochemical urinalysis in a toilet bowl, urinal, or urine collection container, comprising:
 a test platform sized to fit within a urine collection apparatus in the form of one of a toilet bowl, urinal, or urine collection container, the test platform having two or more test wells capable of receiving urine introduced into the urine collection apparatus and automatically distributing required volumes of the urine to each test well, wherein each test well contains electrodes, conductive traces, and chemicals for electro-chemical tests to generate or alter electrical signals in presence of specific urinary analytes or biomarkers over time that is specific to analytes being investigated in a urine sample for disease diagnosis, disease progression monitoring, and/or organ health monitoring, and each test well is capable of testing for a different urinary analyte so that the test platform can simultaneously conduct tests for different analytes, wherein the test platform is made of paper with the electrodes and conductive traces printed on the paper, and the chemicals are provided on the paper, wherein the paper of the test platform is frusto-conical with a larger open top end and a smaller closed bottom end and the entire test platform is flushable; and an electronic reader that receives signals from the test wells in series or simultaneously, converts the signals to data values of analytes or ratios thereof, and is capable of collecting, storing, analyzing, and transmitting the data values to an external electronic device or cloud platform.

2. The system of claim 1, wherein the test platform is configured to be fit capable of fitting within a urine collection container which is a urine collection cup.

3. A method of using electrochemical methods of urinalysis in a toilet bowl, urinal, or urine collection container, comprising:
providing a system for electrochemical urinalysis in a toilet bowl, urinal, or urine collection container, comprising:
a test platform sized to fit within a urine collection apparatus in the form of one of a toilet bowl, urinal, or urine collection container, the test platform having two or more test wells capable of receiving urine introduced into the urine collection apparatus and automatically distributing required volumes of the urine to each test well, wherein each test well contains electrodes, conductive traces, and chemicals for electro-chemical tests to generate or alter electrical signals in presence of specific urinary analytes or biomarkers over time that is specific to analytes being investigated in a urine sample for disease diagnosis, disease progression monitoring, and/or organ health monitoring, and each test well is capable of testing for a different urinary analyte so that the test platform can simultaneously conduct tests for different analytes, wherein the test platform is made of paper with the electrodes and conductive traces printed on the paper, and the chemicals are provided on the paper, wherein the paper of the test platform is frustoconical with a larger open top end and a smaller closed bottom end; and
an electronic reader that receives signals from the test wells in series or simultaneously, converts the signals to data values of analytes or ratios thereof, and is capable of collecting, storing, analyzing, and transmitting the data values to an external electronic device or cloud platform;
introducing urine into the urine collection apparatus;
receiving the signals at the electronic reader;
converting the signals to data, collecting, storing, analyzing and transmitting the data from the electronic reader to the external electronic device or cloud platform; and
monitoring the data at the external electronic device or cloud platform.

4. The system of claim 1, wherein each test well is connected by a channel to a common distribution assembly arranged to collect the urine introduced into the urine collection apparatus.

5. The system of claim 4, wherein the common distribution assembly includes a pumping mechanism and the channels are sized for variable volume distribution.

6. The system of claim 4, wherein the common distribution assembly includes a pumping mechanism through microfluidic channels.

7. The system of claim 1, wherein the test platform comprises at least three test wells.

8. The system of claim 1, wherein each test well has a capacitance sensor mounted therein to measure fluid level in the test well.

9. The system of claim 1, wherein there are differently sized test wells.

10. The system of claim 9, wherein each test well is connected by a channel to a common distribution assembly arranged to collect the urine introduced into the urine collection apparatus, and the channels are sized for variable distribution of the fluid in a given time to the differently sized test wells.

11. The method of claim 3, including the steps of generating, receiving, analyzing and relaying the data over a pre-determined time period up to 24 hours.

12. The method of claim 3, including the steps of generating, receiving, analyzing and relaying the data continuously.

13. The method of claim 3, wherein at least two analytes that require different times to generate or alter electrical signals are analyzed in series to record ratios of the amounts of the two or more analytes.

14. The method of claim 3, wherein at least two analytes requiring different times to generate or alter electrical signals are analyzed simultaneously to record ratios of the amounts of the two or more analytes.

15. The system of claim 1, wherein the chemicals are coated or immobilized on the test wells.

16. The system of claim 1, wherein the paper of the test platform is made of a hydrophobic layer and dissolvable paper.

17. The system of claim 16, wherein any change in the pH caused by the urine reacting with the chemicals and dissolved paper is neutralized by coated chemicals on the paper to allow the test platform to be flushable.

18. The system of claim 1, wherein the electronic reader is a non-disposable electronic device located in proximity to the toilet bowl and connected to the test platform wirelessly.

19. The system of claim 1, wherein the electronic reader is a non-disposable electronic device is mounted to an outside of the toilet bowl and connected to the test platform with wires.

20. A system for electrochemical urinalysis in a toilet bowl, urinal, or urine collection container, comprising:
a test platform sized to fit within a urine collection apparatus in the form of one of a toilet bowl, urinal, or urine collection container, the test platform having two or more test wells, wherein the test wells are differently sized and are capable of receiving urine introduced into the urine collection apparatus and automatically distributing required volumes of the urine to each test well, wherein each test well contains electrodes, conductive traces, and chemicals for electro-chemical tests to generate or alter electrical signals in presence of specific urinary analytes or biomarkers over time that is specific to analytes being investigated in a urine sample for disease diagnosis, disease progression monitoring, and/or organ health monitoring, and each test well is capable of testing for a different urinary analyte so that the test platform can simultaneously conduct tests for different analytes, wherein the test platform is made of paper with the electrodes and conductive traces printed on the paper, and the chemicals are provided on the paper, wherein the paper of the test platform is frustoconical with a larger open top end and a smaller closed bottom end, and the entire test platform is flushable; and
an electronic reader that receives signals from the test wells in series or simultaneously, converts the signals to data values of analytes or ratios thereof, and is capable of collecting, storing, analyzing, and transmitting the data values to an external electronic device or cloud platform, wherein the electronic reader is a non-disposable electronic device mounted to an outside of the toilet bowl and connected to the test platform with wires.

21. The system of claim 20, wherein the test platform is capable of fitting within a urine collection container which is a urine collection cup.

22. The system of claim 20, wherein each test well is connected by a channel to a common distribution assembly arranged to collect the urine introduced into the urine collection apparatus.

23. The system of claim 20, wherein the test platform comprises at least three test wells.

24. The system of claim 20, wherein the chemicals are coated or immobilized on the test wells.

25. The system of claim 20, wherein the paper of the test platform is made of a hydrophobic layer and dissolvable paper.

\* \* \* \* \*